(12) United States Patent
Sanso (10) Patent No.: US 6,735,367 B2
(45) Date of Patent: May 11, 2004

(54) ILLUMINATION LIGHT CONDUCTING OPTICAL-FIBER CONFIGURATION FOR ENDOSCOPE CABLE

(76) Inventor: David W. Sanso, 5529 Willow Springs Dr., Morrison, CO (US) 80243

( * ) Notice: Subject to any disclaimer, the term of this patent is extended or adjusted under 35 U.S.C. 154(b) by 35 days.

(21) Appl. No.: 10/035,357

(22) Filed: Dec. 28, 2001

(65) Prior Publication Data
US 2003/0123825 A1 Jul. 3, 2003

(51) Int. Cl.$^7$ ................................................. G02B 6/06
(52) U.S. Cl. ........................ 385/117; 385/115; 385/116
(58) Field of Search ................................. 385/115, 116, 385/117

(56) References Cited

U.S. PATENT DOCUMENTS

| | | | | |
|---|---|---|---|---|
| 4,529,627 A | * | 7/1985 | Zurbig | 385/117 |
| 5,200,819 A | * | 4/1993 | Nudelman et al. | 348/65 |
| 6,416,234 B1 | * | 7/2002 | Wach et al. | 385/70 |

* cited by examiner

Primary Examiner—Edward J. Glick
Assistant Examiner—Therese Barber
(74) Attorney, Agent, or Firm—J. Preston Oxenham (57) ABSTRACT

An endoscope cable for use in an endoscope viewing apparatus for viewing an objective has an image viewing cable end portion for association with an image viewing device, a distal, image forming end portion including image forming means for forming an image of the objective, an image transmission means for transmitting the image from the image forming means to the image viewing cable end and a plurality of illumination light conducting fibers extending from an illumination light receiving end at the image viewing cable end to an illumination light emitting end at the image forming end of the cable. A first set of the illumination light conducting fibers has an illumination light emitting end portion axis parallel to the cable image forming end portion axis. A second set of the illumination light conducting fibers has an illumination light emitting end portion axis at a first acute angle to the cable image forming end portion axis. A third set of the illumination light conducting fibers has an illumination light emitting end portion axis at a second acute angle to the cable image forming end portion axis.

19 Claims, 5 Drawing Sheets

FIG 1

*PRIOR ART*

FIG 2

*PRIOR ART*

ILLUMINATION LIGHT CONDUCTING OPTICAL-FIBER CONFIGURATION FOR ENDOSCOPE CABLE

TECHNICAL FIELD

The present invention relates to endoscope apparatus and devices for illuminating viewing objectives which are being viewed through endoscope apparatus. More particularly, the present invention relates to endoscopic viewing objective illumination devices which conduct illumination light from a light source at the viewing end of an endoscope apparatus cable to the image forming end of the cable through illumination light conducting optical fibers. Most particularly, the present invention relates to the geometric configuration of such illumination light conducting fibers in proximity to the image forming end of the cable of an endoscope apparatus.

BACKGROUND OF THE INVENTION

Fiber-optic endoscopic viewing systems are now in common use in industrial and medical applications. The use of endoscopic equipment has become commonplace in locksmithing and other industrial applications to allow otherwise hidden mechanical components to be viewed and manipulated. Endoscopic surgical and exploratory procedures are steadily replacing more traditional invasive surgical procedures in contemporary medical practice.

Generally, objects and scenes which are the viewing objective of fiber-optic endoscopic viewing systems are typically in very poorly illuminated or totally dark environments and illumination of the viewing objective must be provided to allow it to be readily observed through the endoscope. Fiber-optic viewing systems of the prior art have utilized flexible, light conducting fiber elements within the endoscope cable to conduct illumination light from a high power light source, such as an incandescent or arc lamp, located at the viewing end of the cable to the distal imaging end of the cable. Typically, each of the illumination light conducting fibers lies adjacent to a central fiber-optic image bundle of the cable with its illumination light conducting fiber axis running generally in set apart parallel relation to the coinciding axes of the endoscope cable and image bundle over the entire length of the endoscope cable. The polished, light emitting end face of each of the illumination light conducting fibers is generally normal to all three axes.

This geometric arrangement of the prior art apparatus does not provide complete and uniform illumination of the viewing field of the image forming device of the fiber-optic image bundle at the image forming end of the endoscope cable. Such image forming devices generally have a conically shaped viewing field expanding with distance from the image forming end of the cable at about a 45 to 50 degree angle to the central cable end axis while light emitted from the face of each of the illumination light conducting fibers is concentrated in a conically shaped illumination field expanding with distance from the end of the fiber at about a 20 degree angle to the central illumination light conducting fiber end axis. Thus, the entire viewing field may not be utilized in viewing distant viewing objectives for lack of sufficient illumination of the viewing objective in the outer portion of the viewing field. Further, the overlapping illumination fields of the illumination light conducting fibers results in nonuniform illumination of the viewing objective within the area of sufficient illumination within the viewing field, most particularly varying with radial distance from the center of the viewing field. Typically, an annular shaped area of relatively intense light is created about the center of the view field.

Some endoscopic viewing systems of the prior art have attempted to mitigate these problems by twisting the distal, image forming end of the endoscope apparatus cable such that the center of the illumination field of each of the illumination light conducting fibers angels outwardly along a chord of the cable cross section at an angle to the cable centerline. While this creates some diffusion of the viewing field illumination, all of the conical illumination fields of the illumination light conducting fibers are displaced at equal angles and an annular area about the center of the view field will still be more intensely illuminated than the rest of the field. Further, constructing an endoscope cable of this configuration is a difficult process.

Other endoscopic viewing systems of the prior art have attempted to mitigate these problems by the placement of small, domed lenses on the light emitting ends of the illumination light conducting fibers. Such lenses may be formed in place by placement of drops of transparent epoxy on the light emitting end surfaces of the fibers. While some diffusion of the illumination light is achieved by these systems, a more intensely illuminated annular area will still exist about the center of the view field.

DISCLOSURE OF THE INVENTION

It is an object of the present invention to provide view objective illumination for an endoscope apparatus utilizing flexible, light conducting fiber elements within an endoscope cable to conduct illumination light from the image viewing end of the cable to the image forming end, which will provide illumination of the entire viewing field It is an object of the present invention to provide view objective illumination for an endoscope apparatus utilizing flexible, light conducting fiber elements within an endoscope cable to conduct illumination light from the image viewing end of the cable to the image forming end, which will provide generally uniform illumination of the view objective along a radius of the viewing field.

It is a further object of the present invention to provide view objective illumination for an endoscope apparatus utilizing flexible, light conducting fiber elements within an endoscope cable to conduct illumination light from the image viewing end of the cable to the image forming end, which will provide uniform illumination of the view objective.

In keeping with the above objectives, an endoscope apparatus comprising a preferred embodiment of the present invention includes an endoscope cable with an image viewing end, and an image forming end with an image forming device. A fiber-optic image bundle extends from the image forming device to the image viewing end of the cable. Sixteen illumination light conducting fiber elements run generally adjacent to, and at equally spaced radial intervals about, the optical-fiber image bundle over the length of the endoscope cable. A light source at the image viewing end of the cable provides light which is conducted by the illumination light conducting fiber elements from the image viewing end of the endoscope cable to the image forming end of the cable where the light is emitted through end faces of the illumination light conducting fiber elements to radiate upon and illuminate the view objective. At the image forming end portion of the endoscope cable, the cable, image forming device and fiber optic image bundle have a common axis including a common image forming end portion axis. Each of the illumination light conducting fiber elements has a central axis including an image forming end portion axis. Four of the illumination light conducting fiber elements, located at equally spaced intervals about the image forming device, have image forming end portion axes which are parallel with the common image forming end portion axis. Four of the illumination light conducting fiber elements, located at equally spaced intervals about the image forming device, and at equally spaced intervals between the first four illumination light conducting elements, have image forming end portion axes which are at a 10 degree angle to the common image forming end portion axis. The remaining eight of the illumination light conducting fiber elements, located at equally spaced intervals about the image forming device, have image forming end portion axes which are at a 20 degree angle to the common image forming end portion axis. Each illumination light conducting fiber element has a polished end face generally normal to its image forming end portion axis.

Other objects, advantages and aspects of the invention will become apparent upon perusal of the following detailed description and claims and upon reference to the accompanying drawings.

DETAILED DESCRIPTION

Figure 1:
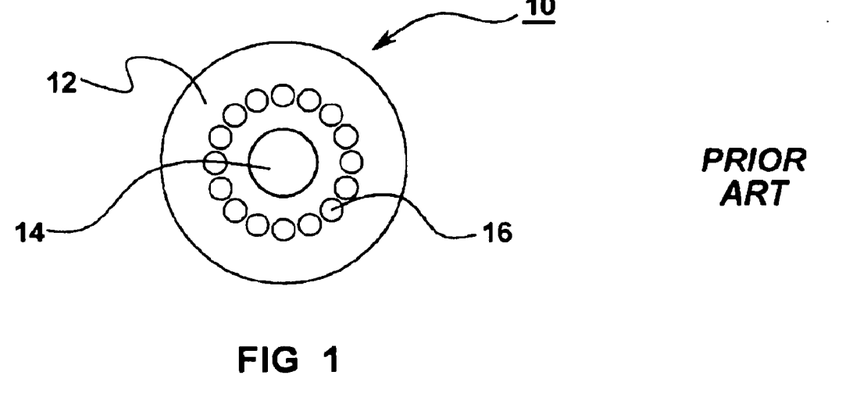
FIG. 1 is an end view of the image forming end of an endoscope cable of an endoscope apparatus of the prior art.
Figure 2:
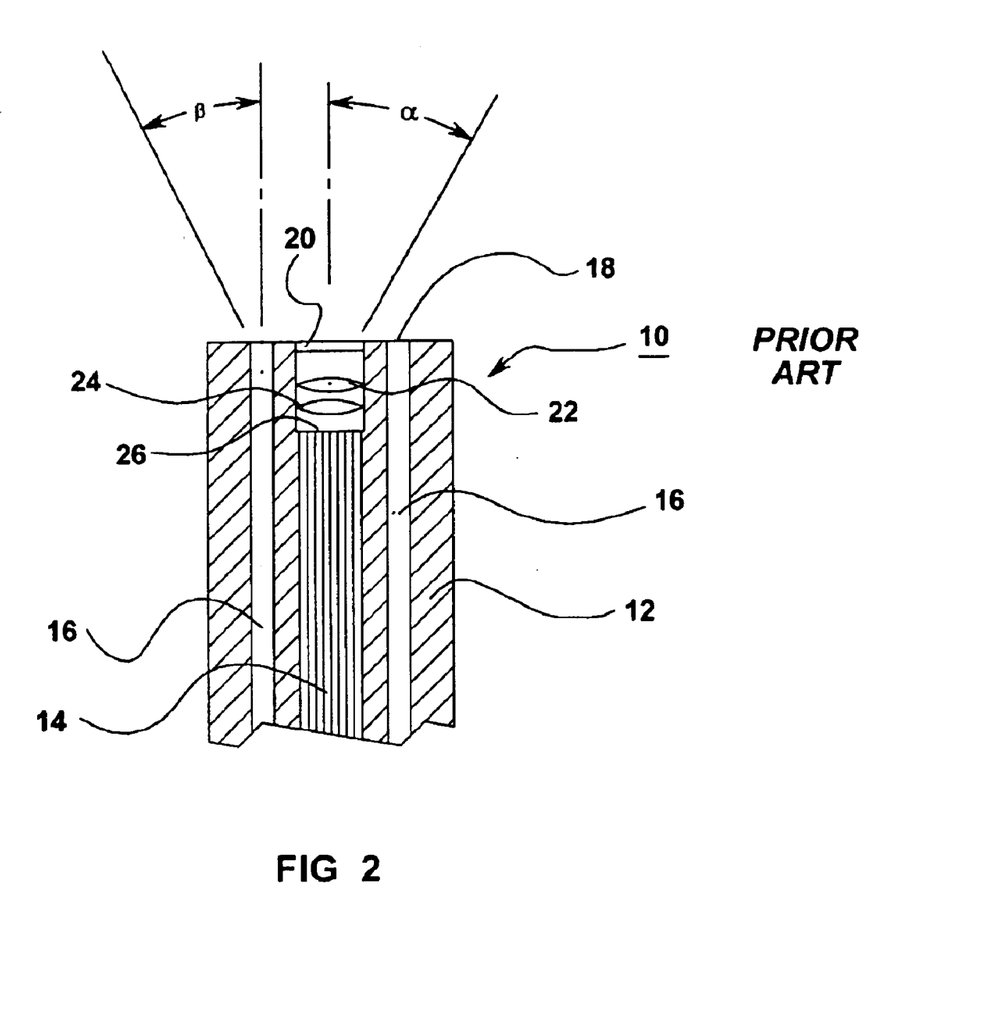
FIG. 2 is a sectional view of an image forming end portion of an endoscope cable of an endoscope apparatus of the prior art.

An end view of a distal image forming end portion of an endoscope cable of an endoscope apparatus of the prior art is shown in FIG. 1. FIG. 2 is a side view, in section, of the distal image forming end portion of endoscope cable 10 of the endoscope apparatus of the prior art shown in FIG. 1. Body 12 of endoscope cable 10 is fabricated of a of a flexible material and encases central fiber-optic image bundle 14 and illumination light conducting fibers 16. As shown in FIG. 1, illumination light conducting fibers 16 typically surround fiber-optic image bundle 14 and image window 20, and lay adjacent to fiber-optic bundle 14 over the length of the cable from its image viewing end to its distal, image forming end. Thus, the central axis of each of illumination light conducting fibers 16 generally lies in set apart parallel relation to the central axis of cable 10 over its entire length. The central axis of the image forming end portion of each of illumination light conducting fibers 16, proximate to end face 18, is generally parallel to the image forming end portion of the common axis of cable 10, fiber-optic image bundle 14 and the image forming device incorporating lenses 22 and 24. When in use, the image viewing end of cable 10 is attached to an endoscope apparatus having a bright light source lamp which radiates light upon the viewing end faces of illumination light conducting fiber elements 16. A portion of the light is conducted by illumination light conducting fibers 16 from the viewing end of the cable, along the length of cable 10 to the image forming end of the cable where the light is emitted from end faces 18 of illumination light conducting fibers 16 to illuminate the endoscopic viewing objective. When the objective is illuminated, light reflected by the objective passes through image window 20 and is focused by imaging lenses 22 and 24 to form an image on imaging end face 26 of image bundle 14. The image is then conducted along fiber-optic image bundle 14 over the length of cable 10 to the viewing end of the cable where it is typically coupled to a television camera to allow display of the image for viewing on an electronic image viewing monitor.

Typically, image forming devices such as the lens assembly of the image forming end of prior art endoscope cable 10 of FIGS. 1 and 2, have a conically shaped viewing field expanding with distance from the end of the cable at an angle $\alpha$ to the central cable image forming end portion axis of about 45 to 50 degrees, while light emitted from the face of each of illumination light conducting fiber faces 18 is concentrated in a conically shaped illumination field expanding with distance from the end of the fiber at an angle $\beta$ to the central fiber portion end axis of about 20 degrees. Thus, the entire viewing field may not be utilized in viewing distant viewing objectives for lack of sufficient illumination of the viewing objective in the outer portion of the viewing field. Further, overlapping of the illumination fields of illumination light conducting fibers 16 results in nonuniform illumination of the viewing objective within the area of sufficient illumination varying both with angular position about the viewing field and, most particularly, with radial distance from the center of the viewing field.

Figure 3:
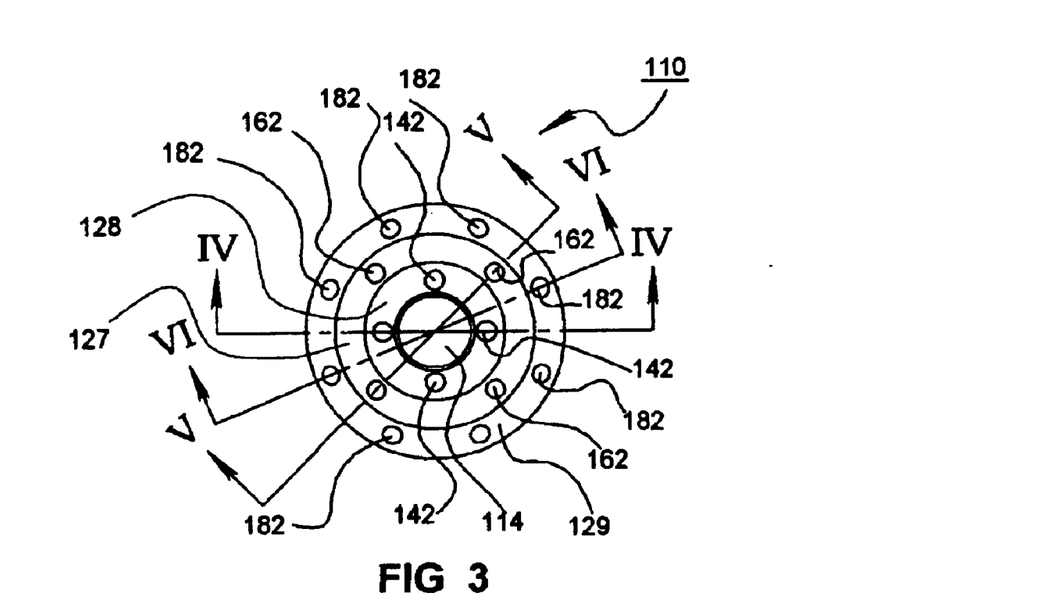
FIG. 3 is an end view of an endoscope cable of an endoscope apparatus comprising a preferred embodiment of the present invention.
Figure 4:
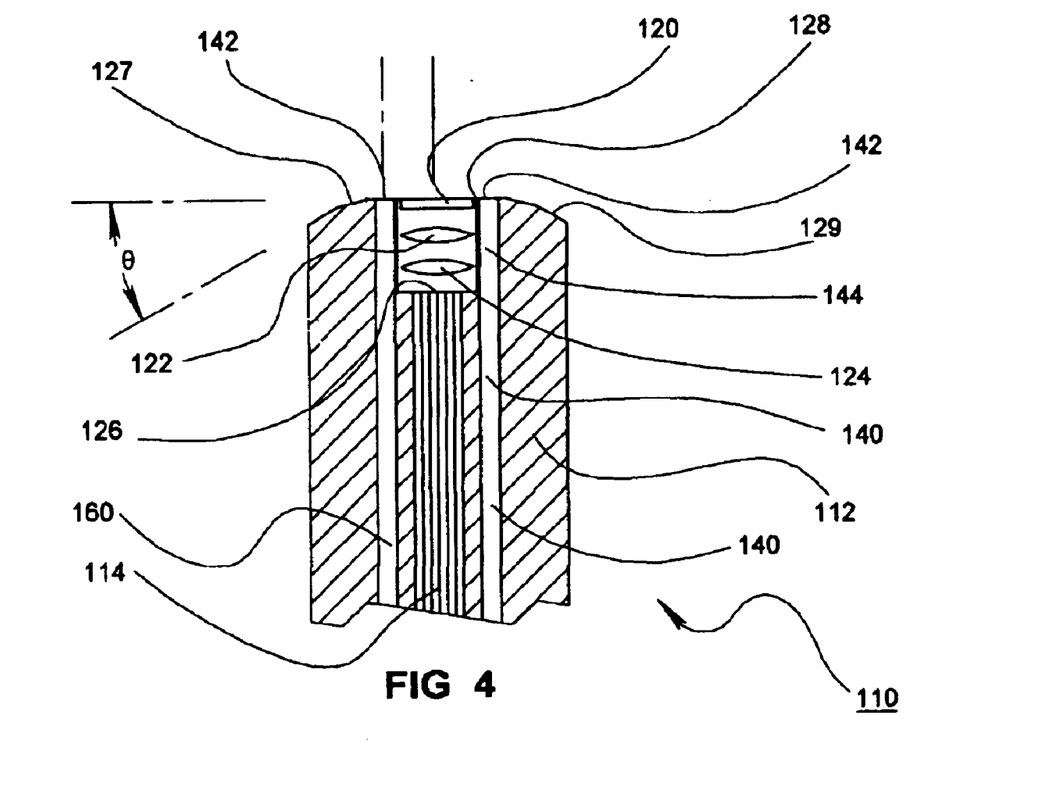
FIG. 4 is a sectional view of an endoscope cable of an endoscope apparatus comprising a preferred embodiment of the present invention taken at plane IV—IV of FIG. 3.
Figure 5:
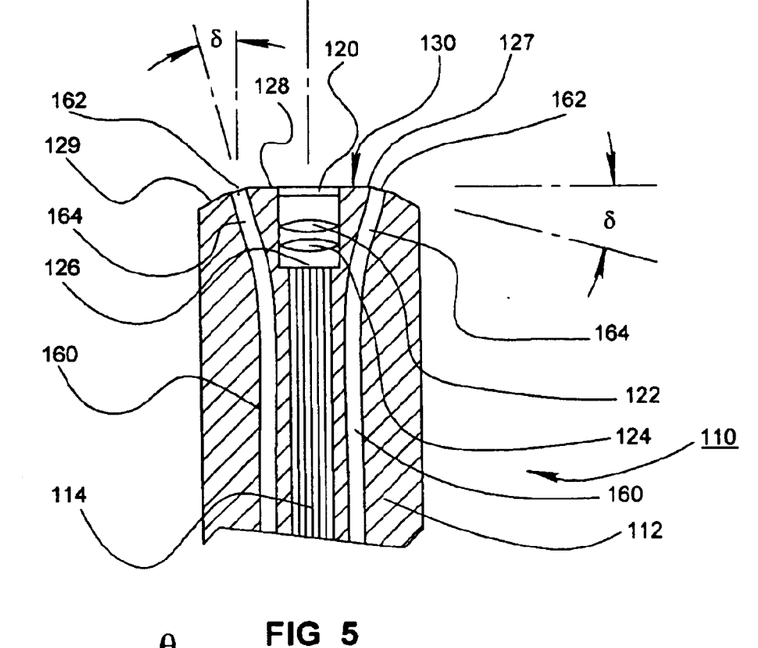
FIG. 5 is a sectional view of an endoscope cable of an endoscope apparatus comprising a preferred embodiment of the present invention taken at plane V—V of FIG. 3.
Figure 6:
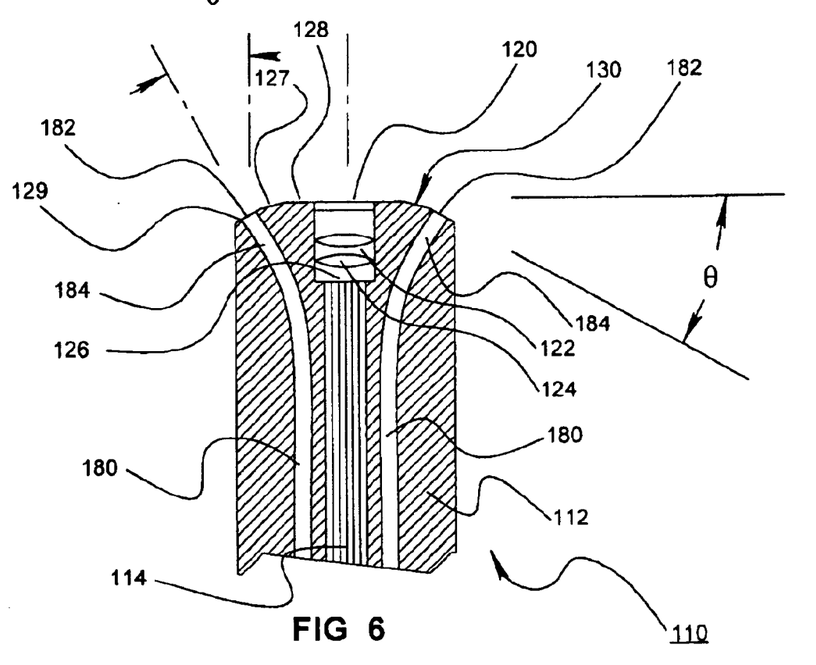
FIG. 6 is a sectional view of an endoscope cable of an endoscope apparatus comprising a preferred embodiment of the present invention taken at plane VI—VI of FIG. 3.

An end view of a distal image forming end portion of an endoscope cable of an exemplary endoscope apparatus comprising a preferred embodiment of the present invention is shown in FIG. 3. FIGS. 4, 5 and 6 are sectional views of the distal image forming end portion of endoscope cable 110 of the exemplary endoscope apparatus comprising a preferred embodiment of the present invention shown in FIG. 3 taken at cutting planes IV—IV, V—V, and VI—VI, respectively, of FIG. 3. Similar elements to the endoscope apparatus cable of FIGS. 1 and 2 are numbered similarly. Similar to the construction of endoscope cable 10, body 112 of endoscope cable 110 is fabricated of a flexible material and encases central fiber-optic image bundle 114. Body 112 of endoscope cable 110 of the preferred embodiment of the present invention also encases 16 illumination light conducting fibers 140, 160 and 180 which extend from the viewing end of endoscope cable 110 to the image forming end of cable 110. Illumination light conducting fibers 140, 160 and 180 all have central axes which are generally parallel to the common axis of cable 110 and central fiber-optic image bundle 114 over the length of the cable.

The central axes of the four illumination light conducting fiber elements 140 of cable 110 of the exemplary endoscope apparatus comprising a preferred embodiment of the present invention are parallel to the central axis of cable 110 over the entire cable length, including the central axis of image forming end portion 144 of each of fibers 140 proximate each end face 142, which are generally parallel to the common axis of fiber-optic image bundle 114 and cable 110, including the image forming device incorporating lenses 122 and 124. The central axes of the four illumination light conducting fiber elements 160 of cable 110 of the exemplary endoscope apparatus comprising a preferred embodiment of the present invention are parallel to the central axis of cable 110 over the cable length from the viewing end of the cable to the image forming end portion. However, the central axis of image forming end portion 164 of each of fibers 160 proximate each end face 162 forms an angle with the common axis of fiber-optic image bundle 114 and cable 110, including the image forming device incorporating lenses 122 and 124. In the preferred embodiment of FIGS. 3 through 6, the angle formed between the axis of each end portion 164 with the common axis is an acute angle, δ, of about 10 degrees. The central axes of the eight illumination light conducting fibers 180 of cable 110 of the exemplary endoscope apparatus comprising a preferred embodiment of the present invention are parallel to the central axis of cable 110 over the cable length from the viewing end of the cable to the image forming end portion. However, the central axis of image forming end portion 184 of each of fibers 180 proximate each end face 182 forms an angle with the common axis of fiber-optic image bundle 114 and cable 110, including the image forming device incorporating lenses 122 and 124. In the preferred embodiment of FIGS. 3 through 6, the angle formed between the axis of each end portion 184 with the common axis is an acute angle, θ, of about 20 degrees.

A viewing end portion of an endoscope cable of the preferred embodiment of the present invention shown in FIGS. 3 through 6 may be constructed by fabricating the main body of the cable in a conventional manner and allowing the illumination light conducting fibers to extend beyond the main body of the cable beyond the point at which it is desired that the completed cable terminate. The image forming end of the main cable body can then be fixed in a jig which is also adapted to engage the individual illumination light conducting fibers at a point beyond the point at which it is desired that the completed cable terminate to hold the fibers under tension at he desired angular position about the central cable axis and at the desired angular position relative to the cable axis. A plug may also be positioned on the end of the fiber-optic image bundle to assist in creating a cavity for an image forming device. The space between and about the drawn illumination light conducting fibers may then be filled sufficiently with a plastic material, such as an epoxy resin, which will harden into a suitably machineable state. Once hardened, the illumination light conducting fibers may be cut, the end surfaces of the cable machined to the desired shape, the plug removed, the image forming device installed, and the illumination light conducting fiber end faces polished to complete fabrication of the cable image forming end portion.

Figure 7:
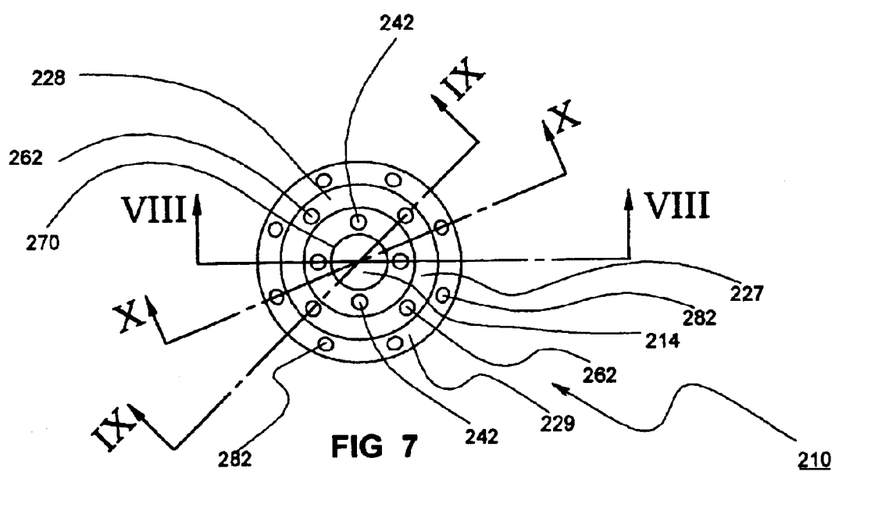
FIG. 7 is an end view of an endoscope cable of an endoscope apparatus comprising an alternative embodiment of the present invention.
Figure 8:
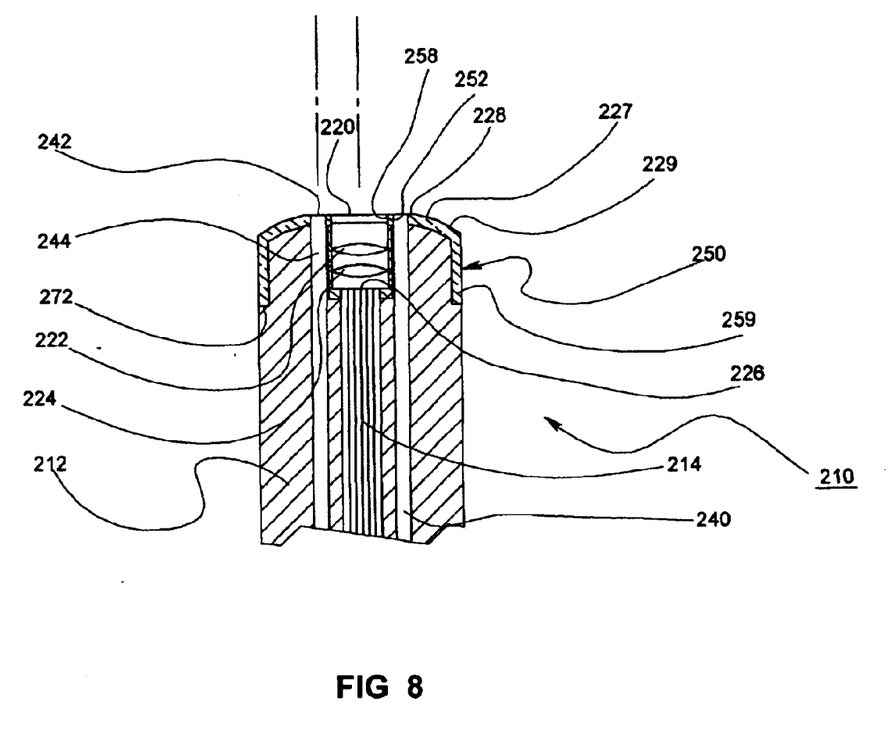
FIG. 8 is a sectional view of an endoscope cable of an endoscope apparatus comprising an alternative embodiment of the present invention taken at plane VIII—VIII of FIG. 7.
Figure 9:
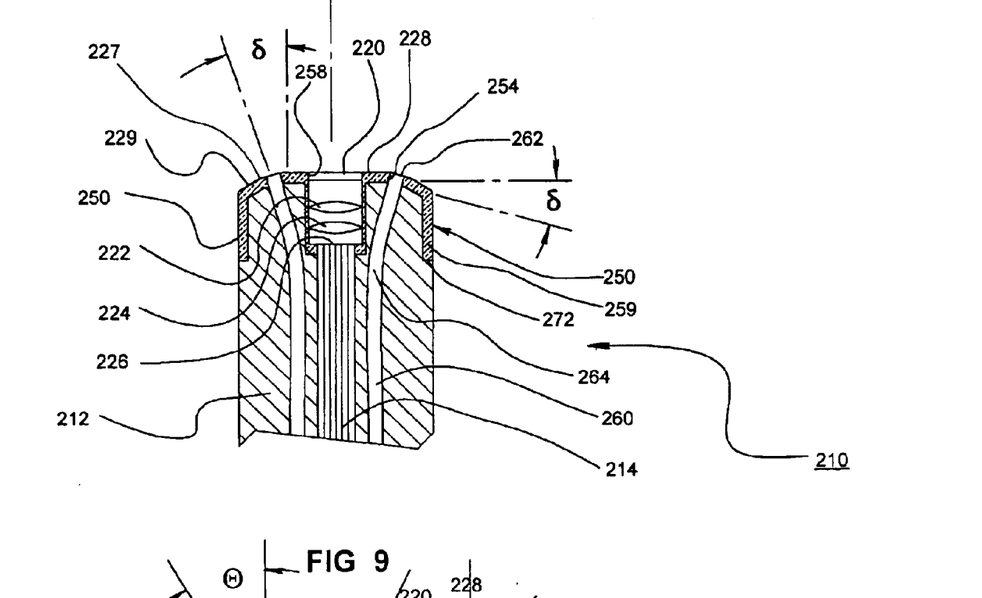
FIG. 9 is a sectional view of an endoscope cable of an endoscope apparatus comprising an alternative embodiment of the present invention taken at plane IX—IX of FIG. 7.
Figure 10:
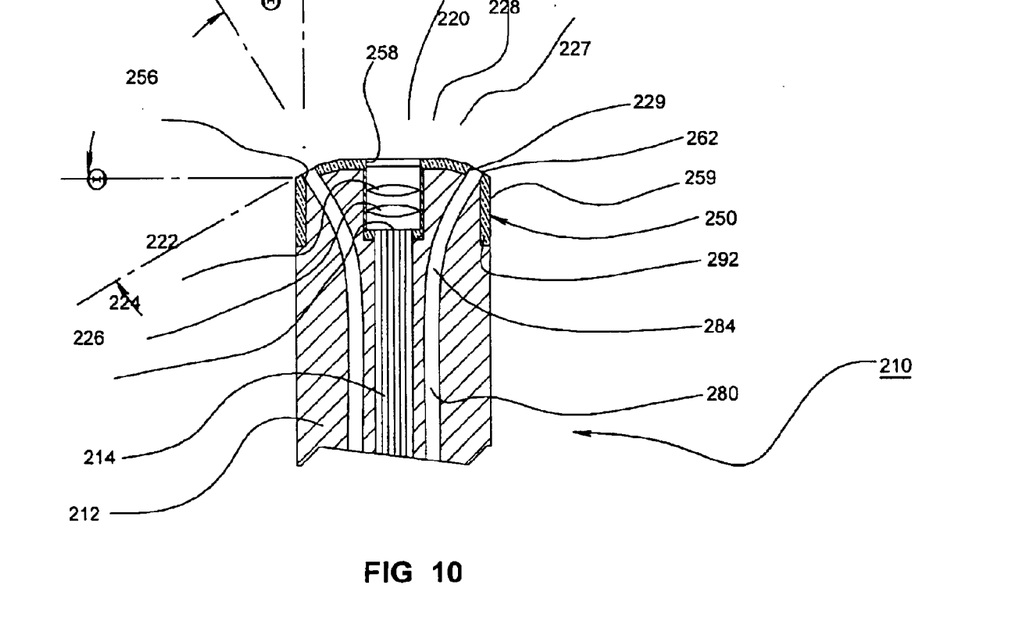
FIG. 10 is a sectional view of an endoscope cable of an endoscope apparatus comprising an alternative embodiment of the present invention taken at plane X—X of FIG. 7.

An end view of a distal image forming end portion of an endoscope cable of an exemplary endoscope apparatus comprising an alternative embodiment of the present invention is shown in FIG. 7. FIGS. 8, 9 and 10 are sectional views of the distal image forming end portion of endoscope cable 210 of the exemplary endoscope apparatus comprising an alternative embodiment of the present invention shown in FIG. 7 taken at cutting planes VIII—VIII, IX—IX, and X—X, respectively, of FIG. 7. Elements similar to those of the earlier disclosed embodiment of FIGS. 3 through 6 are numbered similarly. As in the previous embodiment of FIGS. 3 through 6, body 212 of endoscope cable 210 is fabricated of a flexible material and encases central fiber-optic image bundle 214. Body 212 of endoscope cable 210 of the alternative embodiment of the present invention encases 16 illumination light conducting fibers 240, 260 and 280 which extend from the viewing end of endoscope cable 210 to the image forming end of cable 210. Illumination light conducting fibers 240, 260 and 280 all have central axes which are generally parallel to the common axis of cable 210 and central fiber-optic image bundle 214 over the length of the cable.

As with the earlier, preferred embodiment of FIGS. 3 through 6, the central axes of the four illumination light conducting fiber elements 240 of cable 210 of the exemplary endoscope apparatus comprising an alternative embodiment of the present invention are parallel to the central axis of cable 210 over the entire cable length, including the central axis of image forming end portion 244 of each of fibers 240 proximate each end face 242, which are generally parallel to the common axis of fiber-optic image bundle 214 and cable 210, including the image forming device incorporating lenses 222 and 224. The central axes of the four illumination light conducting fiber elements 260 of cable 210 of the exemplary endoscope apparatus comprising an alternative embodiment of the present invention are parallel to the central axis of cable 210 over the cable length from the viewing end of the cable to the image forming end portion. However, the central axis of image forming end portion 264 of each of fibers 260 proximate each end face 262 forms an angle with the common axis of fiber-optic image bundle 214 and cable 210, including the image forming device incorporating lenses 222 and 224. In the alternative embodiment of FIGS. 7 through 10, the angle formed between the axis of each end portion 264 with the common axis is an acute angle, δ, of about 10 degrees. The central axes of the eight illumination light conducting fibers 280 of cable 210 of the exemplary endoscope apparatus comprising an alternative embodiment of the present invention are parallel to the central axis of cable 210 over the cable length from the viewing end of the cable to the image forming end portion. However, the central axis of image forming end portion 284 of each of fibers 280 proximate each end face 282 forms an angle with the common axis of fiber-optic image bundle 214 and cable 210, including the image forming device incorporating lenses 222 and 224. In the alternative embodiment of FIGS. 7 through 10, the angle formed between the axis of each end portion 284 with the common axis is an acute angle, θ, of about 20 degrees.

End cap 250 of endoscope cable 210 comprising the alternative embodiment of the present invention is made of a rigid material, such as metal or plastic., and covers the image forming end portion of endoscope cable 210. End surface 228 of end cap 250 lies in a plane normal to the axis of the image forming end portion of cable 210 and has an inner edge defining view port 270 to allow light reflected by the viewing objective to enter through image window 220. End surface 228 has four illumination light conducting fiber ports 252 through which end portions 244 of fibers 240 pass such that end faces 242 of fibers 240 conform to surface 228 of end cap 250. Conical surface 227 of end cap 250 is joined to end surface 228 at the outer edge of end surface 228 and is relieved from the plane of surface 228 at angle δ. Conical surface 227 is provided with four illumination light conducting fiber ports 254 through which end portions 264 of fibers 260 pass such that end faces 262 of fibers 260 conform to conical surface 227 of end cap 250. Conical surface 229 of end cap 250 is joined to conical surface 227 at the outer edge of conical surface 227 and is relieved from the plane of surface 228 at angle θ. Conical surface 229 is provided with eight illumination light conducting fiber ports 256 through which end portions 284 of fibers 280 pass such that end faces 282 of fibers 280 conform to conical surface 229 of end cap 250. Cylindrical wall 259 extends from the outer edge of conical surface 229 to an inner edge 272 of end cap 250. Inner edge 272 may be a simple planar circle, as shown in FIGS. 8 through 10, or may be elliptical or even three dimensional, such as a scalloped or surreted edge to assist in maintaining the rotational stability of the cap about the axis of the image forming end portion of cable 210.

A viewing end portion of an endoscope cable of the alternative embodiment of the present invention shown in FIGS. 7 through 10 may be constructed by fabricating the main body of the cable in a conventional manner and allowing the illumination light conducting fibers to extend beyond the main body of the cable beyond the point at which it is desired that the finally formed cable terminate. The image forming end of the main cable body can then be fixed in a jig and image forming device housing 270 fitted to the polished image bundle end face. Illumination light conducting fibers are then fed through illumination light conducting fiber ports 252, 254, and 256 as appropriate as end cap 250 is positioned appropriately in the jig and the illumination light conducting fibers tensioned to correctly position them. A plastic material, such as an epoxy resin, which will harden suitably, is then injected into end cap 250. The illumination light conducting fiber end faces and cap are then polished to complete fabrication of the cable image forming end portion.

While an exemplary endoscope cables comprising a preferred embodiment of the present invention has been shown, it will be understood, of course, that the invention is not limited to those embodiments. Modification may be made by those skilled in the art, particularly in light of the foregoing teachings. For example, rather than bending the distal image forming end portions of the illumination light conducting fibers outwardly from the endoscope cable centerline, prism lenses might be utilized to angle the illumination field centerline of desired fibers from the fiber end portion centerline at desired angles, for example, 10 degrees and 20 degrees. Those familiar with the art will realize that it is also possible to utilize a miniature video camera as the image forming device to transmit an electrical signal to the viewing end of the endoscope cable to be displayed on a video monitor. It is, therefore, contemplated by the appended claims to cover any such modification which incorporates the essential features of this invention or which encompasses the spirit and scope of the invention.

I claim:

1. An endoscope cable for use in an endoscope viewing apparatus for viewing an objective, the cable comprising:
   a cable body having a longitudinal cable body axis;
   an image viewing cable end portion for association with an image viewing means for viewing an image of the objective;
   a distal, image forming cable end portion including image forming means for forming an image of the objective, said image forming cable end portion having an image forming cable end portion axis;
   image transmission means for transmitting an image from said image forming means to said image viewing cable end portion;
   a plurality of illumination light conducting fibers extending from an illumination light receiving end proximate said image viewing cable end portion to an illumination light emitting end proximate said image forming cable end portion, each of said illumination light conducting fibers having an illumination light conducting fiber axis including an illumination light conducting fiber axis light emitting end portion adjacent said illumination light emitting end; and,
   a first of said illumination light conducting fibers has an illumination light conducting fiber axis including a first illumination light conducting fiber axis light emitting end portion and, said first illumination light conducting fiber axis light emitting end portion lies generally parallel to said image forming cable end portion axis; and,
   a second of said illumination light conducting fibers has an illumination light conducting fiber axis including a second illumination light conducting fiber axis light emitting end portion and, an extension of said second illumination light conducting fiber axis light emitting end portion intercepts said image forming cable end portion axis at an acute angle interior of said second illumination light conducting fiber's illumination light emitting end.

2. An endoscope cable as in claim 1, further comprising:
said acute angle is generally 10 degrees.

3. An endoscope cable as in claim 1, further comprising:
said acute angle is generally 20 degrees.

4. An endoscope cable as in claim 1, further comprising:
a third of said illumination light conducting fibers has an illumination light conducting fiber axis including a third illumination light conducting fiber axis light emitting end portion and, an extension of said second illumination light conducting fiber axis light emitting end portion intercepts said image forming cable end portion axis at an acute angle interior of said second illumination light conducting fiber's illumination light emitting end.

5. An endoscope cable as in claim 4, further comprising:
said acute angle is generally 10 degrees; and,
said second acute angle is generally 20 degrees.

6. A cable for an endoscope viewing apparatus as in claim 4, further comprising:
an end cap, said end cap enclosing said distal image forming cable end portion, said end cap including an end face having a planar end face surface with a circular inner edge defining a view port and a circular outer edge, a first conical surface having a circular first conical surface inner edge joined rigidly and continuously to said end face outer edge and a circular first conical surface outer edge, said first conical surface further having a circular first conical surface interior edge defining a first illumination light conducting fiber port adapted to receive said light emitting end portion of said first of said illumination light conducting fibers, said first conical surface relieved from the plane of said planar end surface at an angle equal to said first acute angle such that said first illumination light conducting fiber axis light emitting end portion is normal to said first conical surface, a second conical surface having a circular second conical surface inner edge joined rigidly and continuously to said first conical surface outer edge and a second conical surface outer edge, said second conical surface further having a circular second conical surface interior edge defining a second illumination light conducting fiber port adapted to receive said light emitting end portion of said second of said illumination light conducting fibers, said second conical surface relieved from the plane of said planar end surface at an angle equal to said second acute angle such that said second illumination light conducting fiber axis light emitting end portion is normal to said second conical surface.

7. A cable for an endoscope viewing apparatus as in claim 6, further comprising:

a cylindrical surface having a circular first cylindrical surface edge and a second surface edge, said first cylindrical surface edge joined rigidly and continuously to said second conical surface outer edge.

8. A cable for an endoscope viewing apparatus as in claim 7, further comprising:

said first acute angle is generally 10 degrees; and, said second acute angle is generally 20 degrees.

9. The endoscope cable of claim 1, further comprising:

a central optical fiber image bundle having a central image bundle axis and extending from said distal cable end portion proximate said image forming means to said image viewing cable end portion, said central image bundle axis generally coinciding with the endoscope cable body axis including said image forming cable end portion axis.

10. The improvement of claim 9, further comprising:

said acute angle is generally 10 degrees.

11. The improvement of claim 9, further comprising:

said acute angle is generally 20 degrees.

12. A cable for an endoscope viewing apparatus as in claim 1, further comprising:

an end cap, said end cap enclosing said distal image forming cable end portion, said end cap including an end face having a planar end face surface with a circular inner edge defining a view port and a circular outer edge, a first conical surface having a circular first conical surface inner edge joined rigidly and continuously to said end face outer edge and a circular first conical surface outer edge, said first conical surface further having a circular first conical surface interior edge defining a first illumination light conducting fiber port adapted to receive said light emitting end portion of said first of said illumination light conducting fibers, said first conical surface relieved from the plane of said planar end surface at an angle equal to said first acute angle such that said first illumination light conducting fiber axis light emitting end portion is normal to said first conical surface.

13. In an endoscope cable for use with an endoscope viewing apparatus, the cable including a distal image forming end, a central optical fiber image bundle with an image bundle axis including a distal image bundle axis end portion proximate the image forming end, and illumination light conducting optical fibers lying generally adjacent to the optical fiber image bundle, extending to distal light emitting end faces proximate the image forming end and having central axes including an illumination light conducting optical fiber axis distal end portion proximate the light emitting face, the improvement comprising:

a first of said illumination light conducting fibers has a first illumination light conducting optical fiber axis distal end portion and, said first illumination light conducting optical fiber axis distal end portion lies generally parallel to the distal image bundle axis end portion; and, a second of said illumination light conducting fibers has a second illumination light conducting optical fiber axis distal end portion and, an extension of said second illumination light conducting optical fiber axis light emitting end portion intercepts the distal image bundle axis end portion at an acute angle interior of the distal image forming end.

14. The improvement of claim 13, further comprising:

a third of said illumination light conducting fibers has a third illumination light conducting optical fiber axis distal end portion and, an extension of said third illumination light conducting optical fiber axis light emitting end portion intercepts the distal image bundle axis end portion at a second acute angle interior of the distal image forming end.

15. The improvement of claim 14, further comprising:

said acute angle is generally 10 degrees and said second acute angle is generally 20 degrees.

16. The improvement of claim 14, further comprising:

a first illumination light conducting optical fiber end face is generally normal to said first illumination light conducting optical fiber axis distal end portion; and, a second illumination light conducting optical fiber end face is generally normal to said second illumination light conducting optical fiber axis distal end portion.

17. The improvement of claim 16, further comprising:

said acute angle is generally 10 degrees and said second acute angle is generally 20 degrees.

18. A cable for an endoscope viewing apparatus for viewing an objective, the cable comprising:

a cable body having a longitudinal cable body axis;

an image viewing cable end portion for association with an image viewing means for viewing an image of the objective;

a distal image forming cable end portion including image forming means for forming an image of the objective, said image forming cable end portion having an image forming cable end portion axis coincident with said longitudinal axis;

image transmission means for transmitting an image from said image forming means to said image viewing end portion;

illumination light conducting fibers for conducting illumination light from said image viewing cable end portion to said image forming cable end portion to illuminate a viewing objective, each of said illumination light conducting fibers having an image forming end portion with an image forming end portion axes and a planar end face generally normal to said end portion axis; and, a first of said illumination light conducting fibers has a first image forming end portion axis which intersects said image forming cable end portion axis at a first acute angle at a point on the inner side of the plane of said first illumination light conducting fiber's end face; and, a second of said illumination light conducting fibers has a second image forming end portion axis which intersects said image forming cable end portion axis at a second acute angle at a point on the cable side of the plane of said second illumination light conducting fiber's end face.

19. A cable as in claim 18, further comprising:

said image transmission means includes a fiber-optic image bundle having a central image bundle axis, said image bundle axis generally coinciding with said longitudinal cable axis.

* * * * *